US006530879B1

(12) United States Patent
Adamkiewicz

(10) Patent No.: US 6,530,879 B1
(45) Date of Patent: Mar. 11, 2003

(54) INTRAVAGINAL SET, A METHOD OF TREATMENT OF PROLAPS OF UROGENITAL ORGAN AND URINARY STRESS INCONTINENCE IN WOMEN AND AN APPLICATION OF A INTRAVAGINAL SET

(75) Inventor: Marian Adamkiewicz, Warsaw (PL)

(73) Assignee: Adamed, SP. Z.O.O., Czosnow (PL)

( * ) Notice: Subject to any disclaimer, the term of this patent is extended or adjusted under 35 U.S.C. 154(b) by 0 days.

(21) Appl. No.: 09/303,981

(22) Filed: May 3, 1999

(30) Foreign Application Priority Data

May 4, 1998 (PL) .................................................. 326141

(51) Int. Cl.$^7$ .................................................. A61F 2/02
(52) U.S. Cl. ................... 600/30; 128/885; 128/DIG. 25
(58) Field of Search .............................. 600/29, 30, 38, 600/41, 591; 128/830, 834, 835, 884, 885, DIG. 5; 482/91, 148

(56) References Cited

U.S. PATENT DOCUMENTS 3,938,504 A * 2/1976 Dickinson, III et al.
4,240,412 A * 12/1980 James (List continued on next page.)

FOREIGN PATENT DOCUMENTS

PL             84 12 07          7/1987

OTHER PUBLICATIONS

G. Willy Davila, MD; Vaginal Prolapse "Management with nonsurgical techniques"; Postgraduate Medicine, 99:4:171–185, 1996.

(List continued on next page.)

Primary Examiner—John P. Lacyk
(74) Attorney, Agent, or Firm—Darby & Darby

(57) ABSTRACT

An intravaginal set and a method of treatment of prolaps of urogenital organs and urinary stress incontinence or in the period of intervals in women when the intravaginal therapeutic insert for treatment of static disorders of the urogenital organs and urinary stress incontinence is not currently inserted, said method being realised by means of an intravaginal set of inserts, characterized by selecting the appropriate size of corrective insert from a subset of intravaginal corrective inserts, consisting of at least two balls with step increase in diameter, ranging between the minimal and maximal woman vaginal diameter, each ball being preferably hollow, each ball has the loosely hanging string and each ball is made preferably of medical material, such as polycarbonate or methyl methacrylate, said selecting being realised by means of an intravaginal measuring subset comprising at least two metal or plastic balls having graduated diameters corresponding to graduated diameters of the balls from the subset of the intravaginal corrective inserts, which balls instead of the loosely hanging string have a rigidly mounted linearly scaled slat for measurement of optimal diameter and depth of localization of the corrective insert in the vagina, depending on actual and individual anatomical conditions of urogenital organ of the woman being treated, by the selection of appropriate optimal diameter and depth of localization of the corrective insert in vagina by approximations with using the balls from the measuring subset, so that contraction of the levator ani muscle will cause the elevation of the insert and the elevation of the insert will cause the elevation of the uterus and/or correction of the cysto-urethral angle, and during the progress of said treatment the sizes of successive applied corrective inserts are adjusted by analogic selection of appropriate optimal diameter and depth of localization of the measuring ball in the vagina, and advantageously by carrying out the exercises of the pelvic floor muscles of treated woman lying in prone or genucubital position in the intervals between successive replacements of the corrective inserts.

16 Claims, 3 Drawing Sheets

U.S. PATENT DOCUMENTS

| | | | | |
|---|---|---|---|---|
| 4,574,791 A | * | 3/1986 | Mitchener | |
| 4,785,828 A | * | 11/1988 | Maurer | |
| 5,082,006 A | * | 1/1992 | Jonasson | |
| 5,154,177 A | * | 10/1992 | Eisman et al. | |
| 5,407,412 A | * | 4/1995 | Plevnik et al. | 482/105 |
| 5,864,961 A | * | 2/1999 | Vaughan | 33/512 |
| 5,931,775 A | * | 8/1999 | Smith | 600/29 |

OTHER PUBLICATIONS

A. Martan, et al., "Kolpexin in der konservativen Behandlung der Streβinkotinenz" Zent. bl. Gynakol, 113:645–648, 1991.

Deborah L. Myers, MD, et al. Instruments & Methods, "Double Pessary Use in Grade 4 Uterine and Vaginal Prolapse", Obstetrics & Gynecology, 91:6:1019–1020, 1998.

A. Martan, M. Halska, M. Adamkiewicz, et al.; "Our preliminary experience with Kolpexin in the treatment of urinary stress incontinence"; CS Gynecologie 1991:56, c 9–10:510–514.

* cited by examiner

INTRAVAGINAL SET, A METHOD OF TREATMENT OF PROLAPS OF UROGENITAL ORGAN AND URINARY STRESS INCONTINENCE IN WOMEN AND AN APPLICATION OF A INTRAVAGINAL SET

BACKGROUND OF THE INVENTION

The present invention relates to an intravaginal set, used in the case of prolapse of the urogenital organs and urinary stress incontinence, or during the period when a therapeutic intravaginal insert for treatment of static disorders of the urogenital organs and urinary stress incontinence is not currently inserted and the method of the treatment with usage of this intravaginal set, and application thereof.

Aging and past parturitions result in weakening and elongation of the perineum muscles leading to the prolapse of urogenital organs and other anatomical disorders.

Once extended, muscles become weaker and weaker which subsequently results in progress of prolapse up to transvaginal eversion of the uterus. As the vaginal canal is the "locus minoris resistentiae" in the pelvic floor, walls of the vagina may become the ring of hernia (cystocele, uretrocele and rectocele). In the course of progressive prolapse of urogenital organs, discomfort in lower abdominal part intensifies, from a feeling of "heaviness" to one of pain, and urinary stress incontinence becomes apparent.

Prolapse of the urogenital organs causes a decrease in the distance between the uterine cervix and the vaginal inlet, descent of the anterior wall of the vagina along with the urinary bladder and urethra (the cysto-urethral angle becomes more obtuse), and dislocation of the urethra to outside an operation range of the intra-abdominal pressure.

This results in impaired blood outflow from the urogenital organs due to venous constriction (low-pressure blood vessels).

In less advanced cases of the urogenital prolapse, special therapeutic exercises are recommended to strengthen the pelvic floor muscles.

The physical exercises may only increase the efficiency of the cross-striated muscles, i.e. muscles dependent on the person's own physical characteristics, whereas the urogenital organs equilibrium is independent of the patient's muscle responses since it is controlled by the autonomous nervous system. Strong muscles build the urinary bladder, urethra, internal sphincter muscle of urethra, and muscles in uterine ligaments fix the uterus in its normal position.

A significant progress in the treatment of static disorders of the urogenital organs has been made by development of a therapeutic insert (patent specification No. RP 138406), consisting of a hollow ball with a string attached freely outside the ball, and a smaller ball placed freely inside the hollow ball. This device generates mechanical impulses stimulating contractions of surrounding muscles, both smooth, and cross-striated. A metal ball placed for free movement in the intravaginal therapeutic insert generates mechanical impulses by hitting its cap as a result of translocation to the center of gravity while the patient is walking. The mechanical impulse stimulates muscular contraction. Regular muscular exercise results in muscle hypertrophy and an increase in muscular force. The therapeutic insert may be used twice a day, over a period of about 30 minutes.

Prolonged application longer than 30 minutes leads to muscular overstrain and abdominal pain Use of the therapeutic insert every day over a period of three months achieved satisfactory therapeutic results in the treatment of minor prolapse of the urogenital organs (grade I), while in more advanced cases (grades II, III, IV) no improvement was observed.

The most probable explanation of this result is that in the case of more advanced urogenital prolapse the uterus lowers during intervals between use of the therapeutic device, resulting in unfavorable effects (isometric contraction, passive congestion).

When conservative therapy is ineffective, the reconstructive surgery is performed to restore the normal position of the urogenital organs. Different strategies of therapeutic management are used, depending on symptoms, age and progress of the illness. From among around 200 modifications applied to correct the position of the urogenital organs, the basic management consists in shortening of muscles and ligaments. Such therapeutic management ameliorates the position of the organs, but it does not restore the normal muscular function and thus a lasting and complete recovery.

In the case of contraindications for surgery, a deviceprostheses may be used to ensure a normal position of the urogenital organs.

One such device is the well-known intravaginal disc for support of a lowered or prolapsed uterus. This disc is applied in a manner such that its ring surrounds the uterine cervix, thus preventing uterus prolapse by extension of the vaginal wall in the area of the posterior vaginal fornix. A disadvantage of this design includes difficulties in application and removal. These problems have limited use of this device. Also, as the disc is placed in the upper part of the vagina, it does not transmit the contraction of the levator ani muscle. Thus, the uterus is not elevated. The British patent application discloses a plastic planar arc, the wider arm of which rests on the public symphysis, while the second, narrow arm presses the urethra against the urinary bladder. The maximum time for intravaginal application is 2 hours, which limits the usefulness of this device. The mode of action of this device is local compression of the urethra, which may lead to inflammation and decubitus ulcers.

There is also a well-known disposable vaginal pack (made in Germany), which is placed in the vagina for a period of up to 8 hours. Its mode of action is a mild compression of the urethra and adjustment to the vagina after soaking with water before intravaginal application. This vaginal pack, however, does not provide the desired corrective functions, and may cause an inflammatory state in the case of prolonged intravaginal presence. Soaking with vaginal secretion may result in distension of the vagina leading to progressive prolapse of the uterus and urinary bladder.

OBJECT OF THE INVENTION

The object of the invention is to provide an intravaginal set and a method of treatment using the set to obtain permanent optimal positioning of the uterus and urinary bladder.

BRIEF DESCRIPTION OF THE INVENTION

An intravaginal set is provided to be used in the treatment of prolapse of urogenital organs and urinary stress incontinence, or in the period of intervals in women when the intravaginal therapeutic insert for treatment of static disorders of the urogenital organs and urinary stress incontinence is not currently inserted. The therapeutic insert comprises a hollow plastic ball with string attached and freely moving outside the ball, a smaller ball is placed to be freely movable inside the hollow plastic ball, which smaller ball has a weight adequately adjusted to generate mechanical impulses stimulating alternate contractions of the muscles. The set also includes a subset of intravaginal corrective inserts and an intravaginal measuring subset for determining the size of the insert. The subset of intravaginal corrective inserts has at least two balls of different diameters, ranging between the minimal and maximal woman patent vaginal diameter. Each ball is preferably hollow, and each ball has the loosely hanging string. Each ball is preferably made of medical material, such as polycarbonate or methyl methacrylate, while the intravaginal measuring subset comprises at least two balls made of metal or plastic with graduated diameters corresponding to graduated diameters of the balls of subset of intravaginal corrective inserts. The measuring balls, instead of having the loosely hanging string, have a rigidly mounted, preferably linearly scaled, slat for measurement of optimal diameter and depth of localization of the insert in the vagina, depending on actual and individual anatomical conditions of urogenital organs of the woman being treated.

The invention also is directed to a method of treatment of prolapse of urogenital organs and urinary stress incontinence or in the period of intervals in women when the intravaginal therapeutic insert for treatment of static disorders of the urogenital organs and urinary stress incontinence is not currently inserted, said method being realized by means of an intravaginal set of inserts, characterized by selecting the appropriate size of the corrective insert from a subset of intravaginal corrective inserts, consisting of at least two balls with a different increasing diameter, ranging between the minimal and maximal woman vaginal diameter, each ball being preferably hollow, and each ball has a loosely hanging string and each ball is made preferably of medical material, such as polycarbonate or methyl methacrylate. Selecting a ball is realized by means of an intravaginal measuring subset comprising at least two metal or plastic balls having graduated diameters corresponding to graduated diameters of the balls from the subset of the intravaginal corrective inserts, which balls instead of having the loosely hanging string have a rigidly mounted linearly scaled slat for measurement of optimal diameter and depth of location of the corrective insert in the vagina, depending on actual and individual anatomical conditions of the urogenital organs of the woman being treated, by the selection of appropriate optimal diameter and depth of location of the corrective insert in the vagina by approximations by using the balls from the measuring subset, so that contraction of the levator ani muscle will cause the elevation of the insert and the elevation of the insert will cause the elevation of the uterus and/or correction of the cysto-urethral angle, and during the progress of said treatment, the sizes of successive applied corrective inserts are adjusted by analogous selection of appropriate optimal diameter and depth of location of the measuring ball in the vagina, and advantageously by carrying out the exercises of the pelvic floor muscles of the woman being treated lying in prone or genucubital position in the intervals between successive replacements of the corrective inserts.

An application of an intravaginal set in the treatment of prolapse of urogenital organs and urinary stress incontinence or in the period of intervals in women when the intravaginal therapeutic insert for treatment of static disorders of the urogenital organs and urinary stress incontinence is not currently inserted. A method is realized by means of an intravaginal set of inserts from which the appropriate size corrective insert is selected from a subset of intravaginal corrective inserts, consisting of at least two balls of different diameter, ranging between the minimal and maximal woman vaginal diameter, each ball being preferably hollow and having a loosely hanging string and each ball is made preferably of medical material, such as polycarbonate or methyl methacrylate. The selection is realized by means of an intravaginal measuring subset comprising at least two metal or plastic balls of different diameters corresponding to the diameters of the balls from the subset of the intravaginal corrective inserts, each of which balls of the measuring subset instead of the loosely hanging string has a rigidly mounted linearly scaled slat for measurement of optimal diameter and depth of localization of the corrective insert in the vagina, depending on actual and individual anatomical conditions of urogenital organ of the woman being treated. Selection of appropriate optimal diameter and depth of location of th corrective insert in the vagina is by approximations using the balls from the measuring subset, with the corrective insert selection, so that contraction of the levator ani muscle will cause the elevation of the insert and the elevation of the insert will cause the elevation of the uterus and/or correction of the cysto-urethral angle. During the course of treatment the sizes of successive applied corrective inserts are adjusted by anagogic selection of appropriate optimal diameter and depth of location of the measuring ball in the vagina, and advantageously by carrying out exercises of the pelvic floor muscles of the treated woman lying in a prone or genucubital position in the intervals between successive replacements of the corrective inserts.

An application of the corrective intravaginal insert enables maintaining of the insert in the vagina for an indefinite period of time. The insert diameter, selected by means of the measuring device, should ensure permanent correction of uterine and bladder placement, so that the wall of the vagina is not too tense, and that a mass of lowered organs does not cause prolapse of the insert in the standing position.

Correction of the placement of the urogenital organs and reduction of the isometric contraction of muscles supporting the urogenital organs result in restoration of normal blood supply, allowing the muscles to strengthen and also preventing progressive lowering of the urogenital organs. Correction of the cysto-urethral angle enables control of the micturition.

The corrective insert from the set being the subject of the invention is used in the intervals between applications of the therapeutic insert and exerts a beneficial effect on the muscles by removal of the isometric contraction and better preparation for dynamic contraction following application of the therapeutic insert. An alternating application of the therapeutic insert and the corrective insert enables the treatment of the more advanced cases of the urogenital prolapse and improves results of the therapy up to 80%.

The corrective insert applied alternately with the therapeutic insert is properly adjusted, thus it supports the uterus in its optimal placement and, due to its spherical shape, it may move and turn freely in different directions, thus preventing decubital ulceration.

BRIEF DESCRIPTION OF THE DRAWINGS

The invention will now be described by way of example in more detail with reference to the drawings, wherein.

DETAILED DESCRIPTION OF THE INVENTION

The intravaginal set of the invention includes subset of corrective intravaginal inserts (FIG. 1) being preferably hollow balls 1 of different diameter, ranging between the minimal and maximal vaginal diameter. Each ball 1 has an attached loosely hanging string 2 and is made preferably of a medically acceptable inert plastic, such as polycarbonate or methyl methacrylate.

Figure 1:
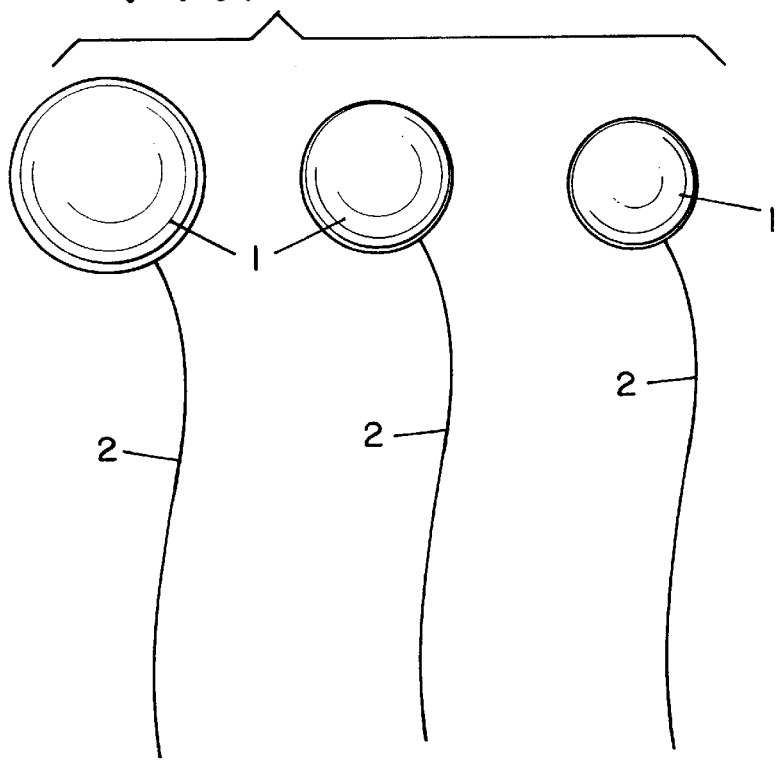
FIG. 1 shows the subset of the corrective intravaginal inserts from the set being the subject of the invention.
Figure 2:
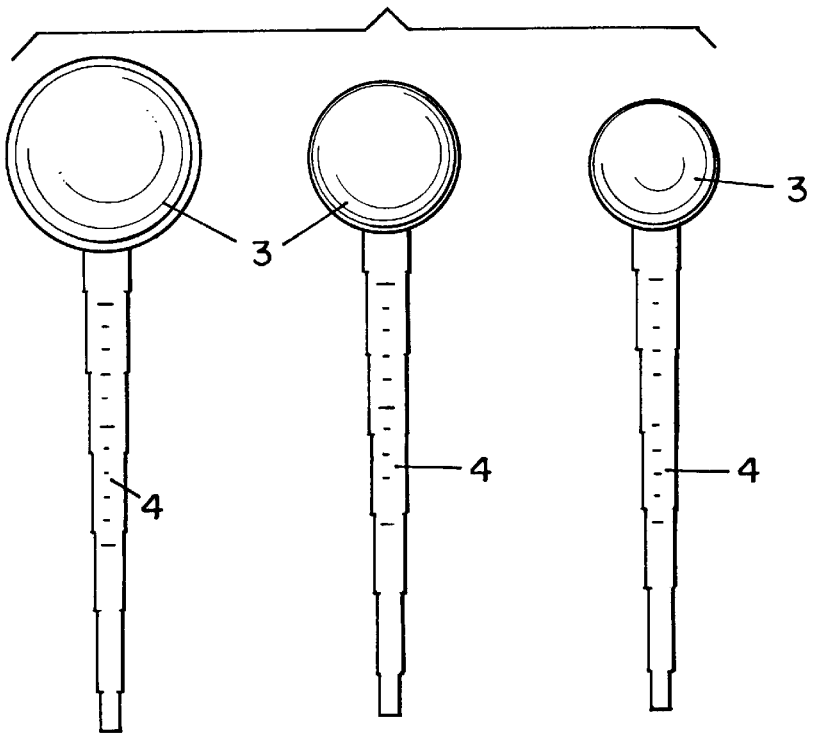
FIG. 2 shows the measuring subset from the set being the subject of the invention.

The set also includes an intravaginal measuring subset (FIG. 2) containing measuring balls 3 made preferably of metal or plastic with graduated diameters corresponding to the graduated diameters of the balls 1 of the subset of corrective intravaginal inserts of FIG. 1. The balls 3 instead of having the loosely hanging string 2, each has a rigidly mounted, linearly scaled slat 4. The slat 4 is preferably scaled for measurement of diameter and optimal location of the corrective insert in the vagina in the case of urinary stress incontinence.

Figure 3:
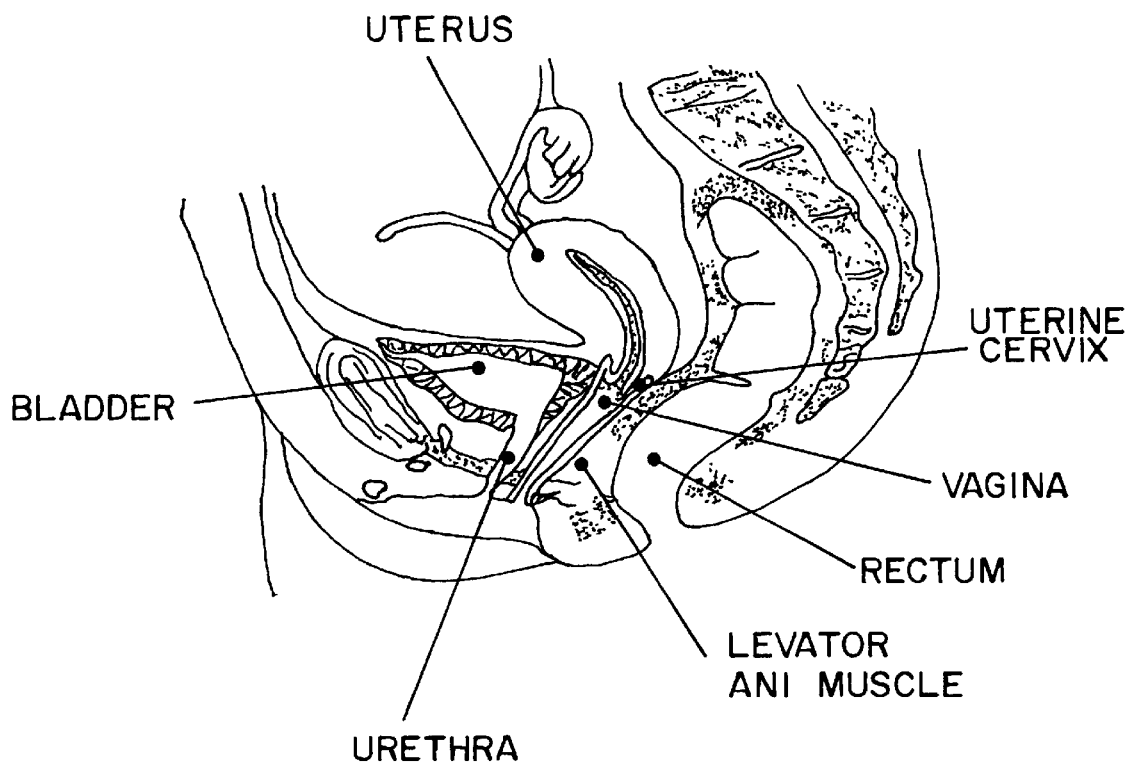
FIG. 3 shows a simplified sagittal cross-section of the female pelvis with the cysto-urethral angle enlarged almost up to 180° when the micturition is started in a controlled or uncontrolled way.

FIG. 3 shows a simplified sagittal cross-section of the female pelvis with the cysto-urethral angle enlarged almost up to 180°, and where the micturition is controlled or involuntary.

Figure 5:
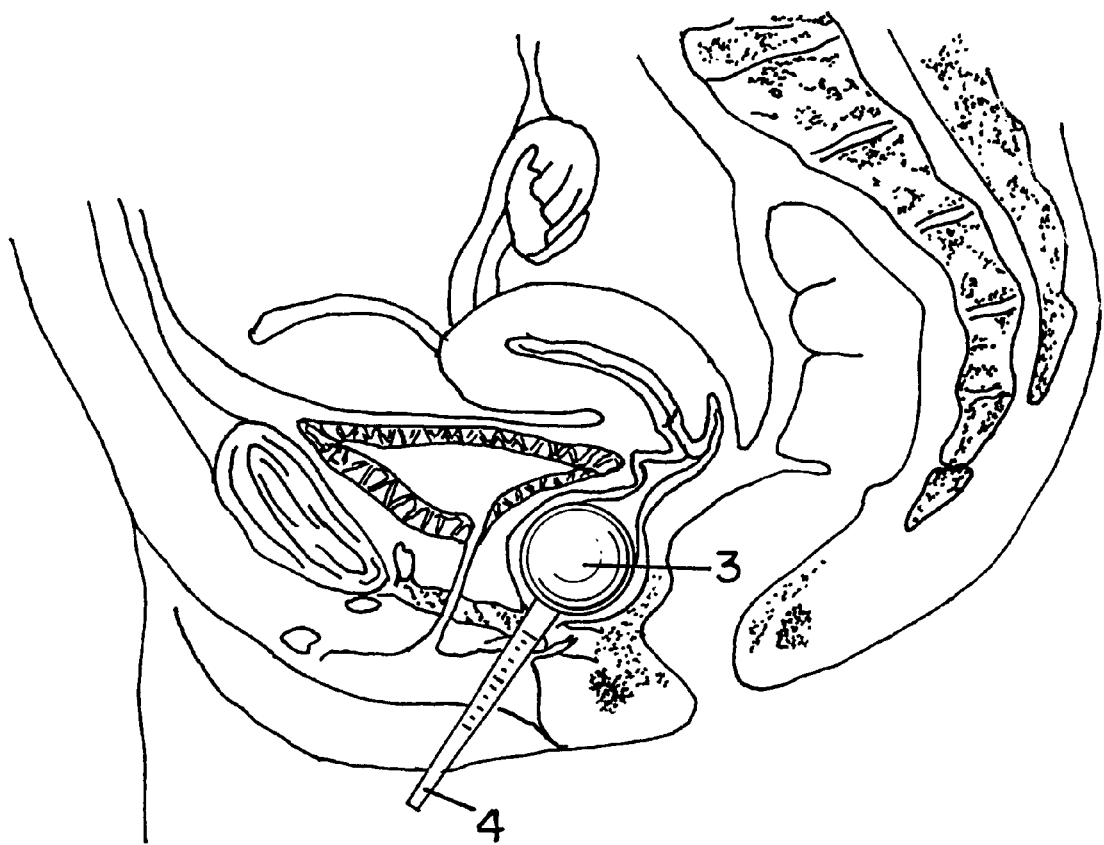
FIG. 5 depicts the method of measuring the diameter of the vagina for determination of optimal location and size of the corrective insert.

FIG. 5 shows the method of measuring the diameter of the vagina using the ball 3 from the measuring subset for determination of depth of location and size of the corrective insert. The appropriate anatomical size is determined using the balls 3 from the measuring subset. Determination is accomplished by checking as to whether an inserted measuring insert is or is not pushed out by the descending organs. If it is not pushed out, a greater insert diameter should be applied. In the case of expulsion, the insert is too large and a smaller diameter insert should be used.

The application of the corrective intravaginal insert involves determination of the optimal diameter of the insert and intravaginal application of the corrective intravaginal insert for an indefinite period of time.

Figure 4:
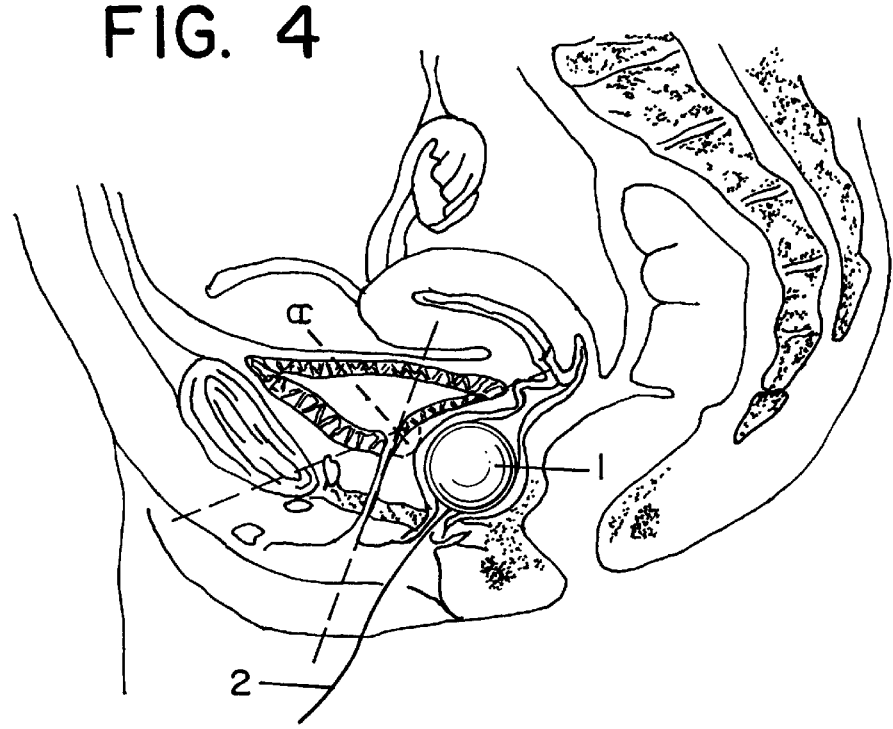
FIG. 4 shows a sagittal cross-section of the female pelvis with the corrective insert from the set being the subject of the invention causing correction of the cysto-urethral angle so that the resulting angle is a right or obtuse angle. At this angle, the mechanism of urethral closure being most effective.

FIG. 4 shows a sagittal cross-section of the female pelvis with the corrective insert of properly selected diameter of the ball 1 by means of the measuring subset. The string 2 is used for removal of the insert.

The mode of action of the insert is as follows. The insert upon being placed in the vagina is supported on the levator ani muscle. It results in forward and upward shift of the lowered anterior wall of the vagina and elevation of the urethra and urinary bladder. An elevation of the urethra restores its normal position in relation to the posterior wall of the urinary bladder (reduced cysto-urethral angle shown on FIG. 4). In the case of concomitant uterine prolapse, the insert causes elevation of the uterus.

Use of the corrective insert of the set of the invention results in fast pain relief. The device also enables a controlled micturition due to correction of the cysto-urethral angle "a" without the necessity to remove the insert for micturition.

Displacement of the uterus to the "pure zone" enables complete removal of inflammation. Relaxation of muscles and fasciae restores normal blood supply of the organs of the pelvis minor. It is most probable that the corrective insert improves results of the treatment with the therapeutic insert. Alternating application of the therapeutic insert and the corrective insert enables the treatment of the more advanced cases of urogenital descent and improves results of the therapy.

The insert can be easily applied and removed. It is supported on the posterior wall of the vagina at the level of the levator ani muscle of anus and thus it prevents excessive extension of the vaginal walls.

The corrective insert from the set being the subject of the invention supports the prolapsed uterus and blocks the urethra in the case of urinary stress incontinence, i.e., inadequate urethral occlusion at increased intra-abdominal pressure. An optimal adjustment of insert diameter to the vagina allows the muscles to regenerate by reduction in uterine and cystic pressure. The corrective insert supports these organs, and after regeneration, the muscles will support the uterus and urinary bladder again, but in a corrected position.

The inventive method of the treatment of prolapse of the urogenital organs and urinary stress incontinence in women with usage of the intravaginal set lies in that the appropriate size corrective insert is selected from the subset of corrective intravaginal inserts, consisting of at least two balls of different diameter, ranging between the minimal and maximal vaginal diameter, each ball being preferably hollow. Each ball has a loosely hanging string and is made of medical material, such as polycarbonate or methyl methacrylate. There is an intravaginal measuring subset that contains at least two metal or plastic balls with diameters corresponding to the diameters of the balls of the corrective intravaginal subset which, instead of the loosely hanging string, each ball has a rigidly mounted, scaled slat for measurement of optimal diameter and localization of the insert in the vagina, depending on individual anatomical conditions of urogenital organ in the woman being treated by selection of the appropriate diameter and depth of vaginal location by means of approximations using the meaning balls from the measuring subset, so that contraction of the levator ani muscle causes elevation of the insert and elevation of the insert causes elevation of the uterus, and/or correction of the cysto-urethral angle. During the progress of treatment the sizes of successive applied inserts are adjusted by selection of appropriate diameter and depth of localization in the vagina and it is beneficial to carry out exercises of the pelvic floor muscles while laying on prone or genucubital position between the successive replacements of the insert.

The size of the applied insert is gradually decreased under medical supervision using the measuring device and ensures permanent correction of uterine and bladder placement by correction of the cysto-urethral angle "a", so that the muscle fibers diffused in surrounding tissue may restore the lowered organs to primary placement.

Size of the applied insert is gradually decreased under medical supervision using the measuring device and ensures permanent correction of uterine and bladder placement by correction of the cysto-urethral angle "a", so that the muscle fibers diffused in surrounding tissue may restore the lowered organs to primary placement.

In the case of significant urogenital prolapse, the uterus is at the same level as the arms of the levator ani muscle, increasing distance between them.

In this case, the corrective intravaginal insert causes an elevation of the uterus, while contractions of the levator ani muscle elevates the insert and, indirectly, the uterus. The corrective insert may fall out at muscular contraction, when its diameter is too small. It is beneficial to make the test for contraction of the levator ani muscle, following an adjustment of the corrective insert by the measuring device.

Exercise of the levator ani muscle with the usage of the corrective insert leads to improved efficiency of the levator ani muscle, vaginal stenosis and elevation of the uterus.

It is necessary to check the position of the insert and the uterus within 2 weeks from the beginning of th recommended exercise.

In advanced cases of urogenital prolapse in which the uterine cervix is placed below the arms of the levator ani muscle, an exercise of the muscle with the usage of the corrective insert elevates the uterus with a decrease in distance between both arms; the insert elevates, resulting in uterine elevation.

Progress in therapy may be monitored using the measuring device for examination of so-called pelvic floor thickness. That is, following insertion, the measuring device is slightly pulled downward to rest it on the arms of the levator ani muscle and the distance from the public symphysis is read from the scaled slat.

An assessment of the therapeutic effect includes repeated measurements of optimal diameter of the corrective insert.

What is claimed is:

1. An intravaginal device for the treatment of prolapse of urogenital organs and urinary stress incontinence, comprising:
    a first set of at least two spherical balls with no internal movable member therein and of different diameters each to be inserted through the vagina to remain in the body above the levator ani muscle to effect treatment, and
    a subset of at least two spherical balls of different diameters corresponding to the diameters of the balls of said first set, each of said balls of said subset having a measuring scale strip attached thereto to determine location of the ball in the body cavity.

2. An intravaginal device as in claim 1 wherein each of said balls of said first set has a string attached thereto to assist in removal of the ball from the body cavity.

3. An intravaginal device as in claim 2 wherein each of said balls of said first set is of plastic.

4. An intravaginal device as in claim 3 wherein said balls of said subset are of plastic or metal.

5. A method of treating prolapse of urogenital organs and urinary stress incontinence by an intravaginal device comprising the steps of:
    providing a first set of at least two spherical balls with no internal movable member therein and of different diameters each to be inserted through the vagina to remain in the body above the levator ani muscle to effect treatment,
    providing a subset of at least two spherical balls of different diameters corresponding to the diameters of the balls of said first set, each of said balls of said subset having a measuring scale strip attached thereto to determine location of the ball in the vagina;
    determining the size and placement location of a spherical ball of said first set to be left in the body by inserting a ball of the subset in the proper location of the vagina;
    removing said ball of said subset; and
    inserting a hollow spherical ball of the first set of the same diameter as that of the ball of the subset removed into the vagina.

6. The method of claim 5 further comprising the steps of:
    removing the ball of said first set from said vagina after a time; and
    replacing it with a ball of said first set of smaller diameter.

7. The method as in claim 6 wherein prior to said replacement step:
    determining the size and placement location of a ball of said first set to be left in the body by inserting a ball of the subset in the proper location of the vagina.

8. The method as in claim 5 further comprising the steps of:
    choosing the appropriate diameter of ball from the first set and inserting it into the vagina above the levator ani muscle for long term insertion, such that the chosen diameter of the ball will reduce the urogenital organs prolapse and will elevate the bladder base and the uterus during pelvic floor exercises.

9. The method of claim 8 further comprising:
    changing the ball of the first set to the progressively smaller one in diameter after regular assessment with the balls of the subset upon strengthening of appropriate muscles and narrowing of the vagina.

10. The method as in claim 9 further comprising:
    performing pelvic floor exercise preferably by contracting the levator ani muscle and squeezing the soft objects between knees in the prone position, preferably twice daily.

11. An intravaginal device for the treatment of prolapse of urogenital organs and urinary stress incontinence, comprising:
    a first set of at least two spherical balls with no internal movable member therein and of different diameters each to be inserted through the vagina to remain in the body above the levator ani muscle to effect treatment.

12. An intravaginal device for the treatment of prolapse of urogenital organs and urinary stress incontinence, comprising:
    a first set of at least two spherical balls with no internal movable member therein and of different diameters each to be inserted through the vagina to remain in the body above the levator ani muscle to effect treatment, and a thread attached to each said ball to permit the ball to be extracted from the vagina by pulling on the thread.

13. An intravaginal device as in claim 1 wherein said spherical balls of said first set are totally hollow.

14. The method of claim 5 wherein said spherical balls of said first set are totally hollow.

15. An intravaginal device as in claim 11 wherein said spherical balls of said first set are totally hollow.

16. An intravaginal device as in claim 15 wherein said spherical balls of said first set are totally hollow.

* * * * *